(12) United States Patent
Bolt et al.

(10) Patent No.: US 8,871,714 B2
(45) Date of Patent: Oct. 28, 2014

(54) HYPERGLYCOSYLATED HUMAN COAGULATION FACTOR IX

(71) Applicant: Novo Nordisk A/S, Bagsvaerd (DK)

(72) Inventors: Gert Bolt, Vaerloese (DK); Claus Kristensen, Nivaa (DK)

(73) Assignee: Novo Nordisk Health Care AG, Zurich (CH)

(*) Notice: Subject to any disclaimer, the term of this patent is extended or adjusted under 35 U.S.C. 154(b) by 0 days.

(21) Appl. No.: 13/723,576

(22) Filed: Dec. 21, 2012

(65) Prior Publication Data

US 2013/0095555 A1 Apr. 18, 2013

Related U.S. Application Data

(63) Continuation of application No. 12/937,331, filed as application No. PCT/EP2009/054707 on Apr. 21, 2009, now abandoned.

(60) Provisional application No. 61/047,605, filed on Apr. 24, 2008.

(30) Foreign Application Priority Data

Apr. 21, 2008 (EP) .................................. 08103629

(51) Int. Cl.
| | | |
|---|---|---|
| *A61K 38/36* | (2006.01) | |
| *C12P 21/04* | (2006.01) | |
| *C07H 21/04* | (2006.01) | |
| *C12N 9/64* | (2006.01) | |

(52) U.S. Cl.
CPC ......... *C12N 9/644* (2013.01); *C12Y 304/21022* (2013.01)
USPC ........................ 514/13.7; 435/69.6; 536/23.5

(58) Field of Classification Search
None
See application file for complete search history.

(56) References Cited

U.S. PATENT DOCUMENTS

| | | | |
|---|---|---|---|
| 6,806,063 | B2 | 10/2004 | Pedersen et al. |
| 7,179,617 | B2 | 2/2007 | DeFrees et al. |
| 2002/0004483 | A1 | 1/2002 | Nissen et al. |
| 2003/0036181 | A1 | 2/2003 | Okkels et al. |
| 2005/0095668 | A1 | 5/2005 | Andersen et al. |
| 2005/0100982 | A1 | 5/2005 | DeFrees et al. |
| 2008/0102115 | A1 | 5/2008 | Oyhenart et al. |
| 2008/0255026 | A1 | 10/2008 | DeFrees et al. |

FOREIGN PATENT DOCUMENTS

| | | |
|---|---|---|
| EP | 0370205 A2 | 5/1990 |
| EP | 640619 A1 | 3/1995 |
| JP | H09-173081 | 7/1997 |
| JP | 2003-519478 A | 6/2003 |

(Continued)

OTHER PUBLICATIONS

Cheng-Mayer et al., "Selection for Neutralization Resistance of the Simian/Human Immunodeficiency Virus SHIVSF33A Variant in Vivo by Virtue of Sequenc Changes in the Extracellular Envelope Glycoprotein That Modify N-Linked Glycosylation", Journal of Virology, 1999, pp. 5294-5300.

(Continued)

*Primary Examiner* — Alexander Kim
(74) *Attorney, Agent, or Firm* — Leon Y. Lum

(57) ABSTRACT

The invention relates to hyperglycosylated human coagulation factor IX polypeptides, to processes for preparing said polypeptides, to pharmaceutical compositions comprising said polypeptides and to the use of the compounds for the treatment of diseases alleviated by human coagulation factor IX, in particular, but not exclusively hemophilia.

4 Claims, 4 Drawing Sheets

(56) References Cited

FOREIGN PATENT DOCUMENTS

| | | |
|---|---|---|
| JP | 2004-534503 A | 11/2004 |
| JP | 2007525941 A | 9/2007 |
| WO | 2004081053 A1 | 9/2004 |
| WO | 2005/024006 A2 | 3/2005 |
| WO | WO/2006/127896 * | 11/2005 |
| WO | 2006/018204 A1 | 2/2006 |
| WO | 2006/127896 A2 | 11/2006 |
| WO | 2007/090584 A1 | 8/2007 |
| WO | 2007/111496 A1 | 10/2007 |
| WO | 2009/051717 A2 | 4/2009 |

OTHER PUBLICATIONS

Elliott et al., "Enhancement of Therapeutic Protein In Vivo Activities Through Glycoengineering", Nature Biotechnology, 2003, vol. 21, pp. 414-421.

Elliott et al., "Control of rHuEPO Biological Activity: The Role of Carbohydrate", Experimental Hematology, 2004, vol. 32, pp. 1146-1155.

Glabe et al., "Glycosylation of Ovalbumin Nascent Chains", Journal of Biological Chemistry, 1980, vol. 255, No. 19, pp. 9236-9242.

Gross et al., "Cellular Trafficking and Degradation of Erythropoietin and Novel Erythropoiesis Stimulating Protein (NESP)", Journal of Biological Chemistry, 2006, vol. 281, pp. 2024-2032.

Jelkmann, "The Enigma of the Metabolic Fate of Circulating Erythropoietin (Epo) in View of the Pharmacokinetics of the Recombinant Drugs rhEpo and NESP", European Journal of Haematology, 2002, vol. 69, pp. 265-274.

Gil et al., "Analysis of the N-Glycans of Recombinant Human Factor IX Purified From Transgenic Pig Milk", Glycobiology, 2008, vol. 18, No. 7, pp. 526-539.

Kiely et al., "Studies on the Attachment of Carbohydrate to Ovalbumin Nascent Chains in Hen Oviduct", Journal of Biological Chemistry, 1976, vol. 251, No. 18, pp. 5490-5495.

Mimuro et al., "Specific Detection of Human Coagulation Factor IX in Cynomolgus Macaques", Journal of Thrombosis and Haemostasis, 2004, vol. 2, No. 2, pp. 275-280.

Perlman et al, "Glycosylation of an N-Terminal E4xtension Prolongs the Half-Life and Increases the In Vivo Activity of Follicle Stimulating Hormone", Journal of Clinical Endocrinology and Metabolism, 2003, vol. 88, pp. 3227-3235.

Schmidt et al., "Structure-Function Relationships in Factor IX and Factor IXa", Trends in Cardiovascular Medicine, 2003, vol. 13, pp. 39-45.

Sinclair et al., Glycoenginee3ring: The Effect of Glycosylation on the Properties of Therapeutic Proteins, Journal of Pharmaceutical Sciences, 2005, vol. 94, No. 8, pp. 1626-1635.

Song et al., "In Vivo Glycosylation Suppresses the Aggregation of Amyloidogenic Hen Egg White Lysozymes Expressed in Yeast", FEBS Letters, 2001, vol. 491, pp. 63-66.

Steen et al., "Functional Characterization of Factor V-Ile359Thr: A Novel Mutation Associated With Thrombosis", Blood, 2004, vol. 103, No. 9, pp. 3381-3387.

Mark J Koury. Trends in Biotechnology. "Sugar Coating Extends Half Lives and Improves Effectiveness of Cyotkine Hormones" 2003. vol. 21(11) pp. 462-464.

Brandtstetter, et al. (1995) "X-Ray structure of clotting factor IXa: active site and module structure related to Xase activity and hemophilia B." Proceedings of the National Academy of Science of the USA vol. 92:9796-9800.

Hopfner et al. (1999) "Coagulation factor IXa: the relaxed conformation of Tyr99 blocks substrate binding" Structure with folding and design vol. 7: 989-96.

* cited by examiner

SEQUENCE LISTING

```
<160> NUMBER OF SEQ ID NOS: 15

<210> SEQ ID NO 1
<211> LENGTH: 415
<212> TYPE: PRT
<213> ORGANISM: Human

<400> SEQUENCE: 1

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255
```

His Asn Tyr Asn Ala Ala Ile Asn Lys Tyr Asn His Asp Ile Ala Leu
                260                 265                 270

Leu Glu Leu Asp Glu Pro Leu Val Leu Asn Ser Tyr Val Thr Pro Ile
            275                 280                 285

Cys Ile Ala Asp Lys Glu Tyr Thr Asn Ile Phe Leu Lys Phe Gly Ser
290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 2
<211> LENGTH: 37
<212> TYPE: DNA
<213> ORGANISM: Artificial Sequence
<220> FEATURE:
<223> OTHER INFORMATION: Synthetic

<400> SEQUENCE: 2
ggataacatc actcaaagca accaatcatt taatgac                    37

<210> SEQ ID NO 3
<211> LENGTH: 37
<212> TYPE: DNA
<213> ORGANISM: Artificial Sequence
<220> FEATURE:
<223> OTHER INFORMATION: Synthetic

<400> SEQUENCE: 3
gtgttgaaac tggtgttaat attacagttg tcgcagg                    37

<210> SEQ ID NO 4
<211> LENGTH: 37
<212> TYPE: DNA
<213> ORGANISM: Artificial Sequence
<220> FEATURE:
<223> OTHER INFORMATION: Synthetic

<400> SEQUENCE: 4
gcaaaagcga aatgtgactc gaattattcc tcaccac                    37

<210> SEQ ID NO 5
<211> LENGTH: 40
<212> TYPE: DNA
<213> ORGANISM: Artificial Sequence
<220> FEATURE:
<223> OTHER INFORMATION: Synthetic

<400> SEQUENCE: 5
ccacaactac aatgcaacta ttaataagta caaccatgac                 40

<210> SEQ ID NO 6
<211> LENGTH: 47
<212> TYPE: DNA
<213> ORGANISM: Artificial Sequence
<220> FEATURE:
<223> OTHER INFORMATION: Synthetic

<400> SEQUENCE: 6
ggataacatc actcaaagca accaatcatt taatgacttc actcggg                47

<210> SEQ ID NO 7
<211> LENGTH: 47
<212> TYPE: DNA
<213> ORGANISM: Artificial Sequence
<220> FEATURE:
<223> OTHER INFORMATION: Synthetic

<400> SEQUENCE: 7
cccgagtgaa gtcattaaat gattggttgc tttgagtgat gttatcc                47

<210> SEQ ID NO 8
<211> LENGTH: 44
<212> TYPE: DNA
<213> ORGANISM: Artificial Sequence
<220> FEATURE:
<223> OTHER INFORMATION: Synthetic

<400> SEQUENCE: 8
gcccactgtg ttgaaactgg tgttaatatt acagttgtcg cagg                   44

<210> SEQ ID NO 9
<211> LENGTH: 44
<212> TYPE: DNA
<213> ORGANISM: Artificial Sequence
<220> FEATURE:
<223> OTHER INFORMATION: Synthetic

<400> SEQUENCE: 9
cctgcgacaa ctgtaatatt aacaccagtt tcaacacagt gggs                   44

<210> SEQ ID NO 10
<211> LENGTH: 44
<212> TYPE: DNA
<213> ORGANISM: Artificial Sequence
<220> FEATURE:
<223> OTHER INFORMATION: Synthetic

<400> SEQUENCE: 10
cagagcaaaa gcgaaatgtg actcgaatta ttcctcacca caac                   44

<210> SEQ ID NO 11
<211> LENGTH: 44
<212> TYPE: DNA
<213> ORGANISM: Artificial Sequence
<220> FEATURE:
<223> OTHER INFORMATION: Synthetic

<400> SEQUENCE: 11
gttgtggtga ggaataattc gagtcacatt tcgcttttgc tctg                   44

<210> SEQ ID NO 12
<211> LENGTH: 47
<212> TYPE: DNA
<213> ORGANISM: Artificial Sequence
<220> FEATURE:
<223> OTHER INFORMATION: Synthetic

```
<400> SEQUENCE: 12
ccacaactac aatgcaacta ttaataagta caaccatgac attgccc                        47

<210> SEQ ID NO 13
<211> LENGTH: 48
<212> TYPE: DNA
<213> ORGANISM: Artificial Sequence
<220> FEATURE:
<223> OTHER INFORMATION: Synthetic

<400> SEQUENCE: 13
gggcaatgtc atggttgtac ttattaatag ttgcattgta gttgtggc                       48

<210> SEQ ID NO 14
<211> LENGTH: 50
<212> TYPE: DNA
<213> ORGANISM: Artificial Sequence
<220> FEATURE:
<223> OTHER INFORMATION: Synthetic

<400> SEQUENCE: 14
gtcttcgatc tacaaagttc aacatcacta acaacatgtt ctgtgctggc                     50

<210> SEQ ID NO 15
<211> LENGTH: 50
<212> TYPE: DNA
<213> ORGANISM: Artificial Sequence
<220> FEATURE:
<223> OTHER INFORMATION: Synthetic

<400> SEQUENCE: 15
gccagcacag aacatgttgt tagtgatgtt gaactttgta gatcgaagac                     50
```

HYPERGLYCOSYLATED HUMAN COAGULATION FACTOR IX

CROSS-REFERENCE TO RELATED APPLICATIONS

This application is a continuation of U.S. Ser. No. 12/937,331, filed Jan. 18, 2011, which is a 35 U.S.C. §371 national stage application of International Patent Application PCT/EP2009/054707, filed Apr. 21, 2009, which claimed priority of European Patent Application 08103629.5, filed Apr. 21, 2008; this application further claims priority under 35 U.S.C §119 of U.S. Provisional Application 61/047,605 filed Apr. 24, 2008; the contents of all above-named applications are incorporated herein by reference.

FIELD OF THE INVENTION

The invention relates to hyperglycosylated human coagulation factor IX polypeptides, to processes for preparing said polypeptides, to pharmaceutical compositions comprising said polypeptides and to the use of the compounds for the treatment of diseases alleviated by human coagulation factor IX, in particular, but not exclusively hemophilia.

BACKGROUND OF THE INVENTION

Coagulation factor IX (FIX) is a vitamin K-dependent coagulation factor with structural similarities to factor VII, prothrombin, factor X, and protein C. The circulating human FIX zymogen consists of 415 amino acids divided into four distinct domains comprising an N-terminal gamma-carboxyglutamic acid rich (Gla) domain, two EGF domains, and a C-terminal trypsin-like serine protease domain. Activation of FIX occurs by limited proteolysis at $Arg^{145}$-$Ala^{146}$ and $Arg^{180}$-$Val^{181}$ releasing a 35 amino acid activation peptide (Schmidt A E, and Bajaj S P (2003) *Trends in Cardiovascular Medicine* 13, 39-45). Wild-type human coagulation factor IX (SEQ ID NO: 1) has two N-glycosylation sites (N157 and N167).

The half-lives of some proteins can be prolonged by adding N-glycans at amino acid positions that are not glycosylated in the wild-type protein (reviewed by Sinclair A M, and Elliott, S (2005) *Journal of Pharmaceutical Sciences* 94, 1626-1635). N-glycans are attached to proteins by eukaryotic cells producing the protein. The cellular N-glycosylation machinery recognizes and glycosylates N-glycosylation signals (N-X-S/T motifs) in the amino acid chain, as the nascent protein is translocated from the ribosome to the endoplasmic reticulum (Kiely et al. (1976) *Journal of Biological Chemistry* 251, 5490-5495; Glabe et al. (1980) *Journal of Biological Chemistry* 255, 9236-9242). Thus, glycoengineered proteins can be produced by introducing mutations that add N-glycosylation sites to the amino acid sequence of the protein. This principle has been employed to obtain longer-acting second generation erythropoietin (Aranesp®, Amgen). This kind of glycoengineering is very attractive in terms of production of the biopharmaceutical, since the final prolonged protein is secreted to the medium of the producer cells. Thus, unlike PEGylation, glycoengineering does not complicate and increase the cost of downstream processing. Furthermore, hyperglycosylation may shield protein epitopes (Cheng-Mayer et al. (1999) *Journal of Virology* 73, 5294-5300) and reduce aggregation by increasing the solubility of the protein (Song et al. (2001) *FEBS Letters* 491, 63-66). In effect, glycoengineering may also improve recombinant proteins by decreasing their immunogenicity, thus reducing the risk that patients develop neutralizing antibodies against the protein.

Interestingly, the influence of N-glycans on clearance varies among different proteins. Several proteins are not influenced by removal or addition of N-glycans. In contrast, some proteins are cleared faster in the absence of their N-glycans and as mentioned above, the clearance of some proteins can be delayed by addition of extra N-glycans (Elliott et al. (2003) *Nature Biotechnology* 21, 414-421; Perlman et al. (2003) *Journal of Clinical Endocrinology and Metabolism* 88, 3227-3235). The mechanisms by which N-glycans influence the clearance of some proteins are unknown and may vary between the proteins. For follicle stimulating hormone, reduced renal clearance due to increased size and increased negative charge from sialic acids has been proposed to explain the delay in clearance induced by extra N-glycans (Perlman et al. (2003), supra). The proteins that are known to be prolonged by addition of extra N-glycans are mostly relatively small proteins, which is in agreement with an effect on renal clearance. For erythropoietin, however, solid evidence for an important role of either renal or hepatic clearance remains to be presented. Intracellular degradation of erythropoietin internalized by cells in the bone marrow after binding to the erythropoietin receptor has been suggested as the major mechanism for clearance of circulating erythropoietin (reviewed by Jelkman, (2002) *European Journal of Haematology* 69, 265-274). The affinity of longer-acting hyperglycosylated erythropoietin to the erythropoietin receptor is reduced compared to wild-type erythropoietin (Elliott et al. (2004) *Experimental Hematology* 32, 1146-1155), and recent evidence suggests a link between the reduced receptor affinity and slower receptor mediated degradation, leading to a longer circulatory half-life (Gross and Lodish, (2006) *Journal of Biological Chemistry* 281, 2024-2032). Interestingly, the reduced receptor binding by hyperglycosylated erythropoietin appears to result from the increased sialic acid content (Elliott et al. (2004) *Experimental Hematology* 32, 1146-1155). The in vitro activity of hyperglycosylated erythropoietin is significantly reduced compared to wild-type erythropoietin, and it is known to a person skilled in the art that a considerable reduction in specific activity must be expected when N-glycans are introduced in proteins at sites that are not glycosylated in the wild-type protein.

US 2003/0036181 (Maxygen, Inc.) describes the addition of glycosylation sites to polypeptides. EP 0640619 (Amgen Inc.) describes erythropoietin analogs with additional glycosylation sites. Mimuro et al. (2004) *Journal of Thrombosis and Haemostasis*, 2, 275-280 describes human coagulation factor IX with the mutation A262T introducing a N-glycosylation site at amino acid position 260.

There is thus a great need for providing an improved variant of human factor IX which demonstrates an increased in vivo circulatory half-life but without dramatically reducing the proteolytic activity or clot activity when compared with wild-type human factor IX.

SUMMARY OF THE INVENTION

According to a first aspect of the invention there is provided a human factor IX polypeptide analogue having one or more mutations wherein said mutations result in the introduction of one or more glycosylation sites in the polypeptide.

According to a second aspect of the invention there is provided a glycosylated human factor IX polypeptide analogue, wherein said polypeptide is glycosylated at one or more positions other than N157 or N167 relative to wild-type human factor IX polypeptide.

According to a further aspect of the invention there is provided a method of treating hemophilia which comprises administering to a patient a therapeutically effective amount of a polypeptide as defined hereinbefore.

DETAILED DESCRIPTION OF THE INVENTION

Figure 1:
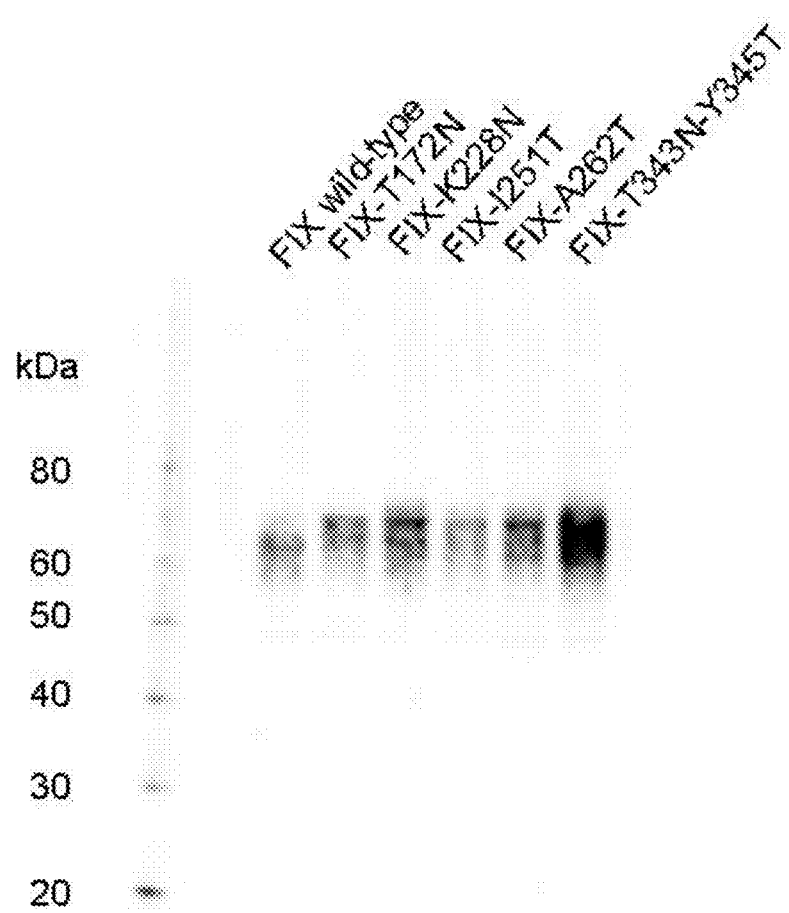
FIG. 1 describes a Western blot of factor IX proteins in medium from HEK293F cells transiently transfected with pTS87 encoding wild-type human coagulation factor IX or with pGB071, pGB072, pGB073, pGB074, or pGB075 encoding hyperglycosylated human coagulation factor IX variants with one N-glycosylation site not present in wild-type human coagulation factor IX (Example 2).

According to a first aspect of the invention there is provided a human factor IX polypeptide analogue having one or more mutations wherein said mutations result in the introduction of one or more glycosylation sites in the polypeptide.

According to a second aspect of the invention there is provided a glycosylated human factor IX polypeptide analogue, wherein said polypeptide is glycosylated at one or more positions other than N157 or N167 relative to wild-type human factor IX polypeptide.

It has been surprisingly found that the hyperglycosylated polypeptide analogues of the present invention demonstrate prolonged circulatory half-life of coagulation factor IX to reduce the dosing frequency and/or increase the exposure of the therapeutic peptide.

The term "protein", "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, y-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (a-aminoisobutyric acid), Abu (a-aminobutyric acid), Tle (tert-butylglycine), β-alanine, 3-aminomethyl benzoic acid and anthranilic acid.

The term "analogue" as used herein referring to a polypeptide means a modified peptide wherein one or more amino acid residues of the peptide have been substituted by other amino acid residues and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. All amino acids for which the optical isomer is not stated are to be understood to mean the L-isomer.

In one embodiment, the one or more mutation results in the introduction of one or more N-glycosylation sites in the polypeptide.

In one embodiment, the one or more mutation results in an increased molecular weight of the factor IX polypeptide analogue when compared with the wild-type polypeptide.

In one embodiment, the one or more mutation results in a more acidic isoelectric point for the factor IX polypeptide analogue when compared with the wild-type polypeptide.

In one embodiment, the one or more mutation results in no more than a 0, 1, 2, 5, 10, 20, 50 or 100 fold reduction of proteolytic activity and/or clot activity of the factor IX polypeptide analogue when compared with the wild-type polypeptide. In a further embodiment, the one or more mutation results in no more than a 0 fold reduction of proteolytic activity and/or clot activity of the factor IX polypeptide analogue when compared with the wild-type polypeptide.

The cellular N-glycosylation machinery glycosylates asparagine residues in N-X-S/T motifs, and potential N-glycosylation sites can be introduced in proteins by amino acid alterations establishing such motifs. Thus, in one embodiment, the mutation within the polypeptide incorporates one or more N-X-S/T motifs. In a further embodiment, the one or more N-X-S/T motifs will preferably be established at positions where the residue to be an "N" has a relative side-chain surface accessibility of more than 25%.

It will be appreciated that surface accessibilities for the heavy chain and EGF2 domain may be calculated from published crystallographic data (1RFN, Hopfner et al. (1999) *Structure with Folding and Design* 7, 989-96), while calculations on the GLA and EGF1 domains may be based on a homology model built from the crystal (and partially modelled) structure of porcine FIXa (1PFX, Brandstetter et al. (1995) *Proceedings of the National Acedemy of Science of the USA* 92, 9796-9800). In addition, the residues in the activation peptide, for which no structural information is available, were considered important. Therefore, in a further embodiment, the residue having a relative side-chain surface accessibility of more than 25% may be selected from one or more of the following:

Y1, S3, G4, F9, V10, Q11, G12, R16, K22, R29, T35, R37, T39, F41, W42, Q44, V46, D47, G48, D49, Q50, E52, S53, N54, L57, N58, G59, S61, K63, D65, I66, N67, S68, Y69, E70, W72, P74, F77, G79, K80, N81, E83, L84, D85, V86, T87, N89, I90, K91, N92, R94, K100, N101, S102, A103, D104, N105, K106, V108, S110, E113, G114, R116, E119, N120, Q121, K122, S123, E125, P126, V128, P129, F130, R134, V135, S136, S138, Q139, T140, S141, K142, A146, E147, A148, V149, F150, P151, D152, V153, D154, Y155, V156, S158, T159, E160, A161, E162, T163, I164, L165, D166, I168, T169, Q170, S171, T172, Q173, S174, F175, N176, D177, F178, T179, R180, G183, E185, D186, K188, P189, K201, V202, D203, E213, E224, T225, G226, K228, E239, E240, T241, H243, K247, N249, I251, R252, I253, P255, H257, N258, N260, A261, A262, I263, N264, K265, A266, D276, E277, P278, V280, N282, S283, Y284, D292, K293, E294, N297, I298, K301, F302, G303, S304, Y306, R312, F314, H315, K316, R317, R318, S319, L321, V322, Y325, R327, P329, L330, D332, R333, A334, T335, L337, R338, K341, F342, T343, Y345, N346, H354, E355, G357, R358, Q362, E372, E374, G375, E388, M391, K392, G393, K394, R403, N406, K409, E410, K411, and K413.

The above mentioned amino acid positions within wild-type human factor IX therefore represent potential targets for introduction of N-glycosylation sites.

Thus, in one embodiment, the one or more mutations, targeting the N-residue having a relative side-chain surface accessibility of more than 25%, may be selected from the group consisting of: Y1N, S3N+K5S/T, G4N+L6S/T, F9N+Q11S/T, V10N+G12S/T, G12N+L14S/T, R16N+C18S/T, K22N, R29N+V31S/T, T35N+R37S/T, R37N, T39N+F41S/T, F41N+K43S/T, W42N+Q44S/T, Q44N+V46S/T, V46N+G48S/T, D47N+D49S/T, G48N+Q50S/T, D49N+C51S/T, Q50N+E52S/T, E52N+N54T, S53N+P55S/T, C56S/T, L57N+G59S/T, G60S/T, S61N+K63S/T, K63N+D65S/T, D65N+N67S/T, I66N+S68S/T, Y69S/T, Y69N+C71S/T, S68N+E70S/T, E70N+W72S/T, W72N+P74S/T, P74N+G76S/T, F77N+G79S/T, G79N+N81S/T, K80N+C82S/T, E83S/T, E83N+D85S/T, L84N+V86S/T, D85N, V86N+C88S/T, T87N+N89S/T, I90N+N92S/T, K91S/T, I90N+N92S/T, K91N+G93S/T, R94S/T, R94N+E96S/T, K100N, A103S/T, S102N+D104S/T, A103N+N105S/T, D104N+K106S/T, V107S/T, K106N+V108S/T, V108N+V110S/T, S110N, E113N+Y115S/T, G114N+R116S/T, R116N+A118S/T, E119N+Q121S/T, K122S/T, Q121N+S123S/T, K122N+C124S/T S123N+E125S/T, E125N+Al25S/T, P126N+V128S/T, V128N+F130S/T, P129N+P131S/T, F130N+C132S/T, R134N, V135N+V137S/T, S136N, S138N, Q139N, T140N+L142S/T, S141N+L143S/T, K142N, A146N+A148S/T, E147N+V149S/T, A148N+F150S/T, V149N+P515S/T, F150N+D152S/T, P151N+V153S/T, D152N+D154S/T, V153N+Y155S/T, D154N+V156S/T, Y155N+N157S/T, V156N, S158N+E160S/T, T159N+A161S/T, E160N+E162S/T, A161N, E162N+I164S/T, T163N+L165S/T, I164N+D166S/T, L165N+N167S/T, D166N+I168S/T, I168N+Q170S/T, T169N, Q170N, S171N+Q173S/T, T172N, Q173N+F175S/T, S174N+N176S/T, F175N+D177S/T, F178S/T, D177N, F178N+R180S/T, T179N+V181S/T, R180N+V182S/T, G183+E185S/T, E185N+A187S/T, D186N+K188S/T, K188N+G190S/T, P189N+Q181S/T, K201N+D203S/T, V202N+A204S/T, D203N+F205S/T, E213N+W215S/T, E224N+G226S/T, T225N+V227S/T, G226N+K228S/T, K228N, E239N, E240N+E242S/T, T241N+H243S/T, H243N+E245S/T, K247N+N249S/T, I251S/T, I251N+I253S/T, R252N+I254S/T, I253N+P255S/T, P255N+H257S/T, H257N+Y259S/T, N260S/T, A262S/T, A261N+I263S/T, A262N+N264S/T, I263N+K265S/T, K265N+N267S/T, A266N+H268S/T, D276N+P278S/T, P278N+V280S/T, E277N+L279S/T, V280N+N282S/T, Y284S/T, S283N+V285S/T, Y284N, D292N+K294S/T, K293N+Y295S/T, E294N, F299S/T, 1298N+L300S/T, K301N+G303S/T, F302N, G303N+G305S/T, S304N+Y306S/T, Y306N+S308S/T, R312N+F314S/T, F314N+K316S/T, H315N+G317S/T, K316N+R138S/T, G317N, R318N+A320S/T, S319N+L321S/T, L321N+L323S/T, V322N+Q324S/T, Y325N+R327S/T, R327N+P329S/T, P329N+V331S/T, L330N+D332S/T, D332N+A334S/T, R333N, A334N+C336S/T, T335N+L337S/T, L337N, R338N, K341N, F342N+I344S/T, T343N+Y345S/T, Y345N+N347S/T, M348S/T, H354N+G356S/T, E355N+G357S/T, G357N+D359S/T, R358N, Q362N+D364S/T, E372N+E374S/T, E374N, G375N, E388N+A390S/T, M391N+G393S/T, K392N+K394S/T, G393N+Y395S/T, K394N+G396S/T, R403N+V405S/T, I4085/T, K409N+K411S/T, E410N, K411N+K413S/T, and K413N.

In a further embodiment, the one or more N-X-S/T motifs will preferably be established at positions where the residue to be an "N" has a relative side-chain surface accessibility of more than 50%. Thus, in one embodiment, the residue having a relative side-chain surface accessibility of more than 50% may be selected from one or more of the following:

Y1, S3, G4, F9, V10, Q11, K22, R37, Q44, V46, D47, G48, Q50, E52, S53, N54, L57, G59, S61, I66, N67, S68, E70, W72, P74, K80, L84, T87, N89, I90, K91, R94, K100, N101, S102, A103, D104, N105, K106, V108, E113, R116, E119, N120, Q121, S123, E125, P129, S138, T140, S141, K142, A146, E147, A148, V149, F150, P151, D152, V153, D154, Y155, V156, S158, T159, E160, A161, E162, T163, I164, L165, D166, I168, T169, Q170, S171, T172, Q173, S174, F175, N176, D177, F178, T179, R180, G183, E185, D186, K188, P189, K201, V202, D203, E224, T225, G226, K228, E239, E240, T241, H243, K247, N249, R252, P255, H257, N260, A261, A262, I263, K265, E277, V280, D292, K293, E294, K301, G303, F314, K316, R318, L321, R327, D332, R333, R338, K341, F342, T343, H354, E355, G357, E372, E374, G375, M391, K392, G393, N406, E410, and K413.

The above mentioned amino acid positions within wild-type human factor IX therefore represent potential targets for introduction of N-glycosylation sites.

Thus, in one embodiment, the one or more mutations, targeting the N-residue having a relative side-chain surface accessibility of more than 50%, may be selected from the group consisting of:

Y1N, S3N+K5S/T, G4N+L6S/T, F9N+Q11S/T, V10N+G12S/T, K22N, R37N, Q44N+V46S/T, V46N+G48S/T, D47N+D49S/T, G48N+Q50S/T, Q50N+E52S/T, E52N+N54T, S53N+P55S/T, C56S/T, L57N+G59S/T, S61N+K63S/T, I66N+S68S/T, Y69S/T, S68N+E70S/T, E70N+W72S/T, W72N+P74S/T, P74N+G76S/T, K80N+C82S/T, L84N+V86S/T, T87N+N89S/T, K91S/T, I90N+N92S/T, K91N+G93S/T, R94N+E96S/T, K100N, A103S/T, S102N+D104S/T, A103N+N105S/T, D104N+K106S/T, V107S/T, K106N+V108S/T, V108N+V110S/T, E113N+Y115S/T, R116N+A118S/T, E119N+Q121S/T, K122S/T, Q121N+S123S/T, S123N+E125S/T, E125N+A125S/T, P129N+P131S/T, S138N, T140N+L142S/T, S141N+L143S/T, K142N, A146N+A148S/T, E147N+V149S/T, A148N+F150S/T, V149N+P515S/T, F150N+D152S/T, P151N+V153S/T, D152N+D154S/T, V153N+Y155S/T, D154N+V156S/T, Y155N+N157S/T, V156N, S158N+E160S/T, T159N+A161S/T, E160N+E162S/T, A161N, E162N+I164S/T, T163N+L165S/T, I164N+D166S/T, L165N+N167S/T, D166N+I168S/T, I168N+Q170S/T, T169N, Q170N, S171N+Q173S/T, T172N, Q173N+F175S/T, S174N+N176S/T, F175N+D177S/T, F178S/T, D177N, F178N+R180S/T, T179N+V181S/T, R180N+V182S/T, G183+E185S/T, E185N+A187S/T, D186N+K188S/T, K188N+G190S/T, P189N+Q181S/T, K201N+D203S/T, V202N+A204S/T, D203N+F205S/T, E224N+G226S/T, T225N+V227S/T, G226N+K228S/T, K228N, E239N, E240N+E242S/T, T241N+H243S/T, H243N+E245S/T, K247N+N249S/T, I251S/T, R252N+I254S/T, P255N+H257S/T, H257N+Y249S/T, A262S/T, A261N+I263S/T, A262N+N264S/T, I263N+K265S/T, K265N+N267S/T, E277N+L279S/T, V280N+N282S/T, D292N+K294S/T, K293N+Y295S/T, E294N, K301N+G303S/T, G303N+G305S/T, F314N+K316S/T, K316N+R138S/T, R318N+A320S/T, L321N+L323S/T, R327N+P329S/T, D332N+A334S/T, R333N, R338N, K341N, F342N+I344S/T, T343N+Y345S/T, H354N+G356S/T, E355N+G357S/T, G357N+D359S/T, E372N+E374S/T, E374N, G375N, M391N+G393S/T, K392N+K394S/T, G393N+Y395S/T, I408S/T, E410N, and K413N.

It will be appreciated that it is more preferable to introduce N-glycosylation sites at locations already holding a N at position 1 or a S/T at position 3. Therefore, in one embodiment, the one or more N-X-S/T motifs will preferably be established at positions where the residue to be an "N" is selected from one or more of the following:

Y1, K22, R37, N54, N58, N67, N81, D85, N89, N92, K100, N101, N105, S110, N120, R134, S136, S138, Q139, K142, V156, A161, T169, Q170, T172, N176, D177, K228, E239, N249, N258, N260, N282, Y284, E294, N297, F302, G317, R333, L337, R338, K341, N346, R358, E374, G375, N406, E410, and K413.

The above mentioned amino acid positions within wild-type human factor IX therefore represent potential targets for introduction of N-glycosylation sites.

Thus, in one embodiment, the one or more mutations, targeting a residue already holding a N at position 1 or a S/T at position 3, may be selected from the group consisting of:

Y1N, K22N, R37N, C56S/T, G60S/T, Y69S/T, E83S/T, D85N, K91S/T, R94S/T, K100N, A103S/T, V107S/T, S110N, K122S/T, R134N, S136N, S138N, Q139N, K142N, V156N, A161N, T169N, Q170N, T172N, F178S/T, D177N, K228N, E239N, I251S/T, N260S/T, A262S/T, Y284S/T, Y284N, E294N, F299S/T, F302N, G317N, R333N, L337N, R338N, K341N, M348S/T, G358N, E374N, G375N, 14085/T, E410N, and K413N.

In a further embodiment, the one or more mutations are selected from one or more of the following:

T172N, K228N, I251T and A262T.

Thus, the one or more glycosylation positions may be selected from:

T172, K228, N249 and N260.

In one embodiment, the one or more mutations do not comprise A262T as a single mutation within the factor IX polypeptide.

In one embodiment, the hyperglycosylated polypeptide comprises at least one glycan.

Peptides and pharmaceutical compositions according to the present invention may be used in the treatment of diseases alleviated by administration of human coagulation factor IX, such as a bleeding disorder e.g. hemophilia, a blood disease, hemarthrosis, hematomas, mucocutaneous bleeding, inherited blood disease, familial bleeding disorder, familial blood disease or factor replacement therapy. In one embodiment, the disease alleviated by administration of human coagulation factor IX is hemophilia, such as hemophilia B or Christmas disease.

Thus according to a further aspect of the invention there is provided a method of treating hemophilia which comprises administering to a patient a therapeutically effective amount of a polypeptide as defined hereinbefore.

There is also provided a polypeptide as defined hereinbefore for use in the treatment of hemophilia.

There is also provided the use of a polypeptide as defined hereinbefore in the manufacture of a medicament for the treatment of hemophilia.

There is also provided a pharmaceutical composition comprising a polypeptide as defined hereinbefore for use in the treatment of hemophilia.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active peptides to prevent the onset of the symptoms or complications. The patient to be treated is preferably a mammal, in particular a human being, but it may also include animals, such as dogs, cats, cows, sheep and pigs. It is to be understood, that therapeutic and prophylactic (preventive) regimes represent separate aspects of the present invention.

A "therapeutically effective amount" of a peptide as used herein means an amount sufficient to cure, alleviate or partially arrest the clinical manifestations of a given disease and its complications. An amount adequate to accomplish this is defined as "therapeutically effective amount". Effective amounts for each purpose will depend on the type and severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

According to a further aspect of the invention there is provided a process for preparing a polypeptide analogue as hereinbefore defined which comprises the steps of:

(a) site directed mutagenesis of human factor IX to incorporate one or more N-X-S/T motifs into DNA encoding human factor IX;

(b) transfection of the resultant nucleic construct into a producer cell; and (c) purification of the polypeptide analogue from the culture medium of the transfected producer cells.

According to a further aspect of the invention there is provided a nucleic acid construct encoding the human factor IX polypeptide analogue as hereinbefore defined.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a peptide of interest. The construct may optionally contain other nucleic acid segments.

A nucleic acid construct of the invention may suitably be of genomic or cDNA origin, for instance obtained by preparing a genomic or cDNA library and screening for DNA sequences coding for all or part of the peptide by hybridization using synthetic oligonucleotide probes in accordance with standard techniques (cf. J. Sambrook et al, 1989, *Molecular Cloning, A Laboratory Manual,* 2d edition, Cold Spring Harbor, N.Y.) and by introducing the relevant mutations as it is known in the art.

A nucleic acid construct of the invention may also be prepared synthetically by established standard methods, e.g. the phosphoamidite method described by Beaucage and Caruthers, Tetrahedron Letters 22, 1859-1869 (1981), or the method described by Matthes et al., EMBO Journal 3, 801-805 (1984). According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or Saiki et al., Science 239, 487-491 (1988).

In one embodiment, the nucleic acid construct of the invention is a DNA construct which term will be used exclusively in the following for convenience. The statements in the following may also read on other nucleic acid constructs of the invention with appropriate adaptions as it will be clear for a person skilled in the art.

In one embodiment, the present invention relates to a recombinant vector comprising a DNA construct of the invention. The recombinant vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector may be an expression vector in which the DNA sequence encoding the peptide of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the peptide.

The promoter may be any DNA sequence which shows transcriptional activity in the host cell of choice and may be derived from genes encoding proteins either homologous or heterologous to the host cell.

The DNA sequence encoding the peptide of the invention may also, if necessary, be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant vector of the invention may further comprise a DNA sequence enabling the vector to replicate in the host cell in question.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 125-130 (1985)), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

According to a further aspect of the invention there is provided a cell transfected with a vector as hereinbefore defined. In one embodiment, the cell is a eukaryotic cell (e.g. a eukaryotic producer cell). In a further embodiment, the cell is a mammalian cell, such as a Chinese Hamster Ovary (CHO) cell (e.g CHO-K1) or a human embryonal kidney (HEK) cell (e.g. HEK293).

According to a further aspect of the invention, there is provided a pharmaceutical formulation comprising a polypeptide as hereinbefore defined.

The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In one embodiment of the invention the pharmaceutical formulation is an aqueous solution.

The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In one embodiment the pharmaceutical formulation is a freeze-dried formulation, whereto the physician or the patient adds solvents and/or diluents prior to use.

In one embodiment the pharmaceutical formulation is a dried formulation (e.g. freeze-dried or spray-dried) ready for use without any prior dissolution.

In one embodiment the invention relates to a pharmaceutical formulation comprising an aqueous solution of a peptide of the present invention, and a buffer, wherein said peptide is present in a concentration from 0.1-100 mg/ml, and wherein said formulation has a pH from about 2.0 to about 10.0.

In one embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In one embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In one embodiment of the invention the formulation further comprises a pharmaceutically acceptable preservative. In one embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof.

In one embodiment of the invention the preservative is present in a concentration from 0.1 mg/ml to 20 mg/ml. In one embodiment of the invention the preservative is present in a concentration from 0.1 mg/ml to 5 mg/ml. In one embodiment of the invention the preservative is present in a concentration from 5 mg/ml to 10 mg/ml. In one embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 20$^{th}$ edition, 2000.

In one embodiment of the invention the formulation further comprises an isotonic agent. In one embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/mi. In one embodiment of the invention the isotonic agent is present in a concentration from 1 mg/ml to 50 mg/ml. In one embodiment of the invention the isotonic agent is present in a concentration from 1 mg/ml to 7 mg/ml. In one embodiment of the invention the isotonic agent is present in a concentration from 8 mg/ml to 24 mg/ml. In one embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 20$^{th}$ edition, 2000.

In one embodiment of the invention the formulation further comprises a chelating agent. In one embodiment of the invention the chelating agent is selected from salts of ethylenediaminetetraacetic acid (EDTA), citric acid, and aspartic acid, and mixtures thereof. In one embodiment of the invention the chelating agent is present in a concentration from 0.1 mg/ml to 5 mg/ml. In one embodiment of the invention the chelating agent is present in a concentration from 0.1 mg/ml to 2 mg/ml. In one embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 20$^{th}$ edition, 2000.

In one embodiment of the invention the formulation further comprises a stabilizer. The use of a stabilizer in pharmaceutical compositions is well-known to the skilled person. For convenience reference is made to Remington: *The Science and Practice of Pharmacy*, 20$^{th}$ edition, 2000.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or mixtures thereof) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In one embodiment of the invention the amino acids or amino acid analogues are used in a concentration, which is sufficient to prevent or delay aggregation of the protein.

In one embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or mixtures thereof) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In one embodiment of the invention the formulation further comprises a stabilizer selected from the group of high molecular weight polymers or low molecular compounds. In one embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In one embodiment of the invention the formulation further comprises a surfactant. In one embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylamonio-1-propanesulfonate, cationic surfactants (quaternary ammonium bases) (e.g. cetyl-trimethylammonium bromide, cetylpyridinium chloride), nonionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 20$^{th}$ edition, 2000.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a peptide of the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the peptide of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nano-particulates, liquid crystals and dispersions thereof, L2 phase and dispersions there of, well known to those skilled in the art of phase behaviour in lipid-water systems, polymeric micelles, multiple emulsions, self-emulsifying, self-micro-emulsifying, cyclodextrins and derivatives thereof, and dendrimers.

Compositions of the current invention are useful in the formulation of solids, semisolids, powder and solutions for pulmonary administration of a peptide of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres and nanoparticles.

Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the peptide of the present invention in the form of a nasal or pulmonal spray. As a still further option, the pharmaceutical compositions containing the peptide of the present invention can also be adapted to transdermal administration, e.g. by needle-free injection or from a patch, optionally an iontophoretic patch, or transmucosal, e.g. buccal, administration.

The invention will now be described with reference to the following non-limited Examples:

EXAMPLES

Example 1

Generation of Expression Constructs Encoding Hyperglycosylated Human Coagulation Factor IX with one N-glycosylation Site not Present in Wild-type Human Factor IX Constructs encoding hyperglycosylated human coagulation factor IX were generated by site-directed mutagenesis of pTS87 consisting of pTT5 with an insert encoding wild-type human coagulation factor IX. Thus, pTS87 encodes human coagulation factor IX with N-glycosylation sites at amino acid residues 157 and 167. pTS87 was mutated with the QuikChange Site-Directed Mutagenesis kit (Stratagene) as recommended by the manufacturer using the forward and reverse primer pairs shown in Table 1. The plasmids generated by the mutagenesis procedure were transformed into competent E. coli, and plasmids from selected clones screened for mutations by DNA sequencing.

This way the constructs pGB071, pGB072, pGB073, pGB074, and pGB075 described in Table 2 each encoding human coagulation factor IX with one N-glycosylation site not present in wild-type human coagulation factor IX were established.

TABLE 1

Mutagenesis primers (altered nucleotides underlined)
and the amino acid alterations induced by the mutations

| Amino acid alteration | Mutagenesis primer pairs |
|---|---|
| T172N | Forward primer (SEQ ID NO: 6):<br>5'-GGATAACATCACTCAAAGCA<u>A</u>CCAATCATTTAATGACTTCACTCGGG-3'<br><br>Reverse primer (SEQ ID NO: 7):<br>5'-CCCGAGTGAAGTCATTAAATGATTGG<u>T</u>TGCTTTGAGTGATGTTATCC-3' |
| K228N | Forward primer (SEQ ID NO: 8):<br>5'- GCCCACTGTGTTGAAACTGGTGTTAA<u>T</u>ATTACAGTTGTCGCAGG-3'<br><br>Reverse primer (SEQ ID NO: 9):<br>5'- CCTGCGACAACTGTAAT<u>A</u>TTAACACCAGTTTCAACACAGTGGG-3' |

TABLE 1-continued

Mutagenesis primers (altered nucleotides underlined)
and the amino acid alterations induced by the mutations

| Amino acid alteration | Mutagenesis primer pairs |
|---|---|
| I251T | Forward primer (SEQ ID NO: 10):<br>5'- CAGAGCAAAAGCGAAATGTGA<u>C</u>TCGAATTATTCCTCACCACAAC-3'<br><br>Reverse primer (SEQ ID NO: 11):<br>5'- GTTGTGGTGAGGAATAATTCGA<u>G</u>TCACATTTCGCTTTTGCTCTG-3' |
| A262T | Forward primer (SEQ ID NO: 12):<br>5'- CCACAACTACAATGCA<u>A</u>CTATTAATAAGTACAACCATGACATTGCCC-3'<br><br>Reverse primer (SEQ ID NO: 13):<br>5'- GGGCAATGTCATGGTTGTACTTATTAATAG<u>T</u>TGCATTGTAGTTGTGGC-3' |
| T343N-Y345T | Forward primer (SEQ ID NO: 14):<br>5'- GTCTTCGATCTACAAAGTTCA<u>AC</u>ATC<u>AC</u>TAACAACATGTTCTGTGCTGGC-3'<br><br>Reverse primer (SEQ ID NO: 15):<br>5'- GCCAGCACAGAACATGTTGTTA<u>GT</u>GATG<u>TT</u>GAACTTTGTAGATCGAAGAC-3' |

TABLE 2

Amino acid alterations relative to wild-type human coagulation factor IX and potential N-glycosylation sites in wild-type or hyperglycosylated human coagulation factor IX encoded by constructs

| Construct | Amino acid alterations | 157 | 167 | 172 | 228 | 249 | 260 | 343 |
|---|---|---|---|---|---|---|---|---|
| pTS87 | — | + | + | − | − | − | − | − |
| pGB071 | T172N | + | + | + | − | − | − | − |
| pGB072 | K228N | + | + | − | + | − | − | − |
| pGB073 | I251T | + | + | − | − | + | − | − |
| pGB073 | A262T | + | + | − | − | − | + | − |
| pGB075 | T343N – Y345T | + | + | − | − | − | − | + |

Example 2

Transient Expression in Mammalian HEK293 Cells of Hyperglycosylated Human Coagulation Factor IX with One N-glycosylation Site not Present in Wild-type Human Factor IX Suspension adapted human embryonal kidney (HEK293F) cells (Freestyle, Invitrogen) were transfected with the pTS87 expression plasmid encoding wild-type human coagulation factor IX or the pGB071, pGB072, pGB073, pGB074, and pGB075 constructs encoding hyperglycosylated human coagulation factor IX per manufacturer's instructions. Briefly, 30 pg of each plasmid was incubated for 20 min with 40 μl 293fectin (Invitrogen) and added to 3×10$^7$ cells in a 125 ml Erlenmeyer flask with serum free Freestyle 293 Expression Medium supplemented with vitamin K. The transfected cells were incubated in a shaking incubator (37° C., 8% $CO_2$ and 125 rpm). Four days after transfection, the cells were pelleted, and the serum free medium was harvested. The cells were resuspended in ulbecco's MEM (Invitrogen) supplemented with fetal calf serum and vitamin K, and incubated in a shaking incubator. The next day, the cells were pelleted, and the medium containing serum was harvested.

Figure 2:
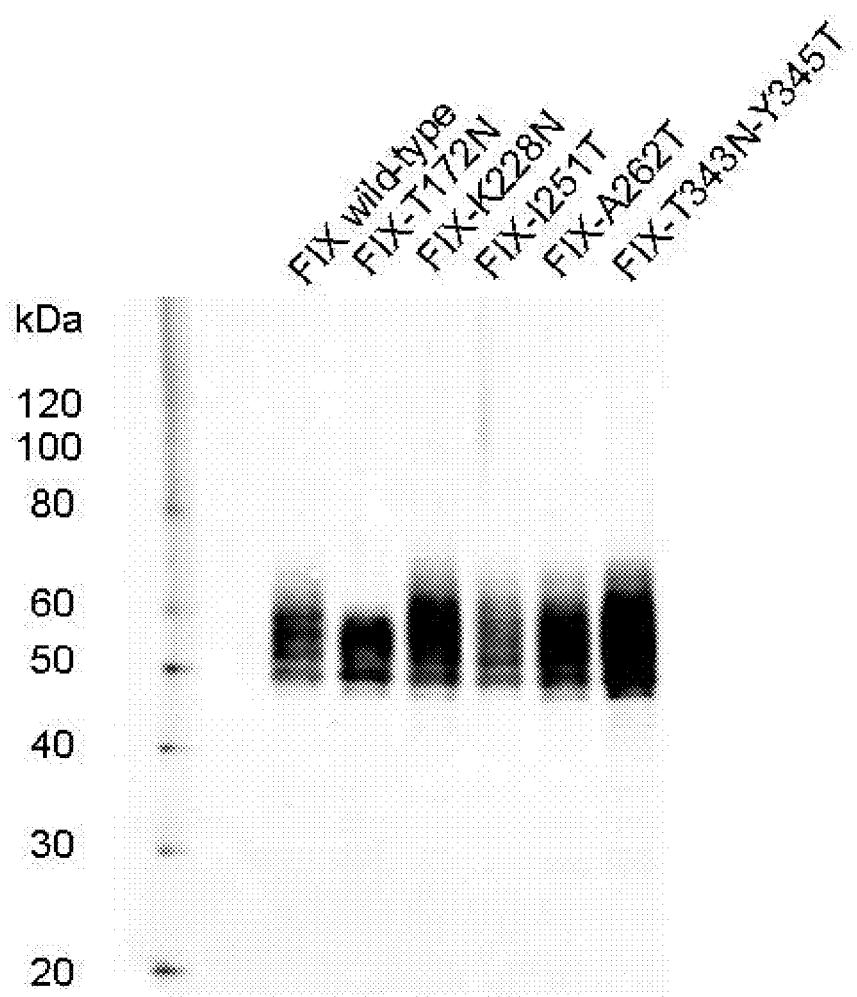
FIG. 2 describes a Western blot of the same media as shown in FIG. 1 upon PNGase F treatment (Example 2).

Samples of the harvested serum free media were incubated 1 h at 37° C. with or without peptide: N-glycosidase F (PNGase F) and loaded on SDS-PAGE gels and electrophoresed. After electrophoresis, the proteins in the gel were transferred to a PVDF membrane by electroblotting. Coagulation factor IX on the membrane was visualized by sequential incubation of the membrane with rabbit anti-FIX antibody and IRDye 680 conjugated goat anti-rabbit IgI (LI-COR). Reading was carried out with an Odyssey scanner (LI-COR) at 680 nm. Readings of membranes are shown in FIG. 1 (samples incubated with PNGase F) and FIG. 2 (samples incubated with PNGase F). The electrophoretic mobilities of the coagulation factor IX variants secreted by cells transfected with pGB071, pGB072, pGB073, pGB074, or pGB075 were reduced compared to the wild-type coagulation factor IX secreted by cells transfected with pTS87 (FIG. 1). PNGase F removes N-linked glycans, and the mobilities of the mutated and the wild-type coagulation factor IX proteins were equalized upon PNGase F treatment (FIG. 2), demonstrating that the different electrophoretic mobilities of the wild-type and variant FIX proteins prior to PNGase F treatment is related to the N-glycans. Thus, hyperglycosylated human coagulation factor IX was indeed produced by cells transfected with pGB071, pGB072, pGB073, pGB074, or pGB075. This demonstrates the utilization of the N-glycosylation sites introduced at amino acid position 172, 228, 249, 260, and 343 in the 5 FIX variants, respectively.

Samples of the harvested media containing serum were analyzed for coagulation factor IX activity by activated partial thromboplastin time (APTT) assay in an ACL 9000 clotting instrument (Instrumentation Laboratory) using reagent from the same manufacturer. The same media were also analyzed for coagulation factor IX antigen content by enzyme-linked immunosorbent assay, and the specific activities of the coagulation factor IX proteins in the media were calculated by combining the ELISA and clot assay data as shown in Table 3. The specific activities of the coagulation factor IX variants with extra N-glycosylation sites at position 172, 228, 249, or 260 were equal to or moderately reduced compared to the specific activity of wild-type human coagulation factor IX. Thus, N-glycans at these positions were not particularly harmful for the clot activity of human coagulation factor IX. In contrast, the specific activity of the FIX-T343N-Y354T variant was dramatically reduced compared to the specific activity of wild-type human coagulation factor IX.

TABLE 3

Characterization of wild-type and hyperglycosylated human coagulation factor IX in medium from transiently transfected HEK293 cells

| Construct | Variant | Factor IX activity (APTT assay) | Factor IX antigen (ELISA) | Specific activity |
|---|---|---|---|---|
| pTS87 | Wild-type FIX | 0.356 U/ml | 5585 ng/ml | 0.06 mU/ng |
| pGB071 | FIX-T172N | 0.258 U/ml | 4879 ng/ml | 0.05 mU/ng |
| pGB072 | FIX-K228N | 0.295 U/ml | 8565 ng/ml | 0.03 mU/ng |
| pGB071 | FIX-I251T | 0.222 U/ml | 4072 ng/ml | 0.05 mU/ng |
| pGB071 | FIX-A262T | 0.206 U/ml | 8228 ng/m | 0.03 mU/ng |
| pGB071 | FIX-T343N-Y345T | 0.007 U/ml | 46636 ng/m | <0.01 mU/ng |

Example 3

Generation of Expression Constructs Encoding Hyperglycosylated Human Coagulation Factor IX with more than One N-glycosylation Site not Present in Wild-type Human Factor IX Constructs encoding hyperglycosylated human coagulation factor IX were generated by site-directed mutagenesis of pTS87 consisting of pTT5 with an insert encoding wild-type human coagulation factor IX. Thus, pTS87 encodes human coagulation factor IX with N-glycosylation sites at amino acid residues 157 and 167. pTS87 was mutated with the QuikChange Multi Site-Directed Mutagenesis kit (Stratagene) as recommended by the manufacturer using the primers shown in Table 4. The plasmids generated by the mutagenesis procedure were transformed into competent *E. coli*, and plasmids from selected clones screened for mutations by DNA sequencing. This way the constructs pGB019, pGB020, pGB021 and pGB022 described in Table 5 each encoding human coagulation factor IX with at least two N-glycosylation site not present in wild-type human coagulation factor IX were established.

The hyperglycosylated human coagulation factor IX encoding nucleotide sequence in pGB022 was subcloned by insertion into the Eco RI site of pMPSVHE to create the plasmid pGB024.

TABLE 4

Mutagenesis primers (altered nucleotides underlined) and the amino acid alterations induced by the mutations

| Amino acid alteration | Mutagenesis primer |
|---|---|
| T172N | 5'-GGATAACATCACTCAAAGCAACCAATCATTTAATGAC-3' (SEQ ID NO: 2) |
| K228N | 5'-GTGTTGAAACTGGTGTTAATATTACAGTTGTCGCAGG-3' (SEQ ID NO: 3) |
| I251T | 5'-GCAAAAGCGAAATGTGACTCGAATTATTCCTCACCAC-3' (SEQ ID NO: 4) |
| A262T | 5'-CCACAACTACAATGCAACTATTAATAAGTACAACCATGAC-3' (SEQ ID NO: 5) |

TABLE 5

Amino acid alterations relative to wild-type human coagulation factor IX and potential N-glycosylation sites in wild-type or hyperglycosylated human coagulation factor IX encoded by constructs

| Construct | Amino acid alterations | 157 | 167 | 172 | 228 | 249 | 260 |
|---|---|---|---|---|---|---|---|
| pTS87 | — | + | + | − | − | − | − |
| pGB019 | T172N + K228N | + | + | + | + | − | − |
| pGB020 | T172N + A262T | + | + | + | − | − | + |
| pGB021 | T172N + K228N + A262T | + | + | + | + | − | + |
| pGB022 | T172N + K228N + I251T + A262T | + | + | + | + | + | + |
| pGB024 | T172N + K228N + I251T + A262T | + | + | + | + | + | + |

Example 4

Figure 3:
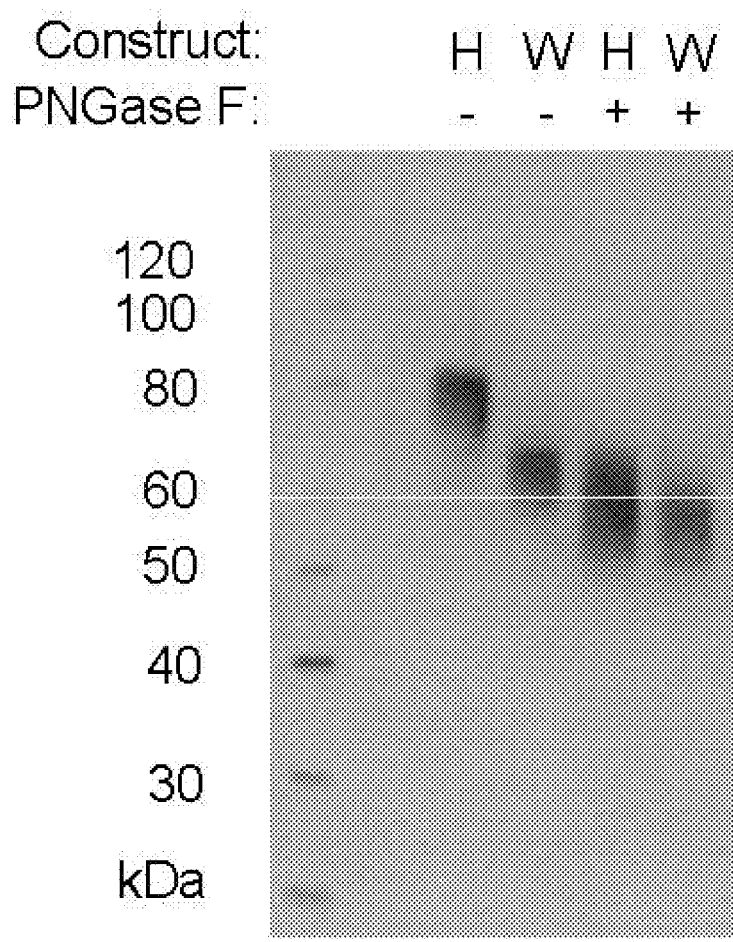
FIG. 3 describes a Western blot of factor IX proteins in medium from HEK293F cells transiently transfected with pGB022 encoding hyperglycosylated (H) human coagulation factor IX (FIX-T172N-K228N-I251T-A262T) or pTS87 encoding wild-type (W) human coagulation factor IX. The media were incubated with or without PNGase F prior to SDS-PAGE (Example 4).

Transient Expression in Mammalian HEK293 Cells of Hyperglycosylated Human Coagulation Factor IX with more than One N-glycosylation Site not Present in Wild-type Human Factor IX Suspension adapted human embryonal kidney (HEK293F) cells (Freestyle, Invitrogen) were transfected with the pTS87 expression plasmid encoding wild-type human coagulation factor IX or the pGB022 construct encoding hyperglycosylated human coagulation factor IX per manufacturer's instructions. Briefly, 30 µg of each plasmid was incubated for 20 min with 40 µl 293fectin (Invitrogen) and added to $3 \times 10^7$ cells in a 125 ml Erlenmeyer flask with Freestyle 293 Expression Medium supplemented with vitamin K. The transfected cells were incubated in a shaking incubator (37° C., 8% $CO_2$ and 125 rpm). Medium harvested 4 days after transfection was incubated 1 h at 37° C. with or without peptide: N-glycosidase F (PNGase F) and was loaded on SDS-PAGE gels and electrophoresed. After electrophoresis, the proteins in the gel were transferred to a PVDF membrane by electroblotting. Coagulation factor IX on the membrane was visualized by sequential incubation of the membrane with rabbit anti-FIX antibody and HRP-conjugated swine anti-rabbit IgG antibody (DAKO) followed by incubation with ECL Western Blotting Detection Reagent (Amersham Biosciences). Reading was carried out with a Las-1000 Luminescent image analyzer (Fujifilm) and is shown in FIG. 3. The electrophoretic mobility of the coagulation factor IX secreted by cells transfected with pGB022 was reduced compared to the wild-type coagulation factor IX secreted by cell transfected with pTS87. PNGase F removes N-linked glycans, and the mobilities of the mutated and wild-type coagulation factor IX proteins upon PNGase F treatment demonstrate that the different electrophoretic mobilities of the two proteins prior to PNGase F treatment is related to the N-glycans. Thus, hyperglycosylated human coagulation factor IX was indeed produced by cells transfected with pGB022.

Example 5

Determination of the Clot Activity of Hyperglycosylated Human Coagulation Factor IX with more than One N-glycosylation Site not Present in Wild-type Human Factor IX Transiently Expressed in Mammalian HEK293 Cells Suspension adapted human embryonal kidney (HEK293F) cells (Freestyle, Invitrogen) were transfected with the pTS87 expression plasmid encoding wild-type human coagulation factor IX or the pGB022 construct encoding hyperglycosylated human coagulation factor IX per manufacturer's instructions. Briefly, 30 µg of each plasmid was incubated 20 min with 40 µl 293fectin (Invitrogen) and added to 3×10$^7$ cells in a 125 ml Erlenmeyer flask with Freestyle 293 Expression Medium (Invitrogen) supplemented with vitamin K. The transfected cells were incubated in a shaking incubator (37° C., 8% $CO_2$ and 125 rpm). Two days after transfection, the medium was replaced with Dulbecco's MEM (Invitrogen) supplemented with fetal calf serum and vitamin K. The cultures were incubated in a shaking incubator two days more, and medium was harvested. The media were analyzed for coagulation factor IX activity by activated partial thromboplastin time (APTT) assay in an ACL 9000 clotting instrument (Instrumentation Laboratory) using reagent from the same manufacturer. The media were also analyzed for coagulation factor IX antigen content by enzyme-linked immunosorbent assay, and the specific activities of the coagulation factor IX proteins in the media were calculated by combining the ELISA and clot assay data as shown in Table 6. The specific activity of the hyperglycosylated coagulation factor IX variant with extra N-glycosylation sites at position 172, 228, 249, and 260 encoded by pGB022 was moderately reduced compared to the specific activity of wild-type human coagulation factor IX. Thus, the presence of up to 4 extra N-glycans at selected amino acid positions are not particularly harmful—for the clot activity of human coagulation factor IX.

TABLE 6

Characterization of wild-type and hyperglycosylated human coagulation factor IX in medium from cells transiently transfected with pTS87 and pGB022, respectively

| Construct | Factor IX activity (APTT assay) | Factor IX antigen (ELISA) | Specific activity |
|---|---|---|---|
| pTS87 | 0.232 U/ml | 2260 ng/ml | 0.10 mU/ng |
| pGB022 | 0.065 U/ml | 1700 ng/ml | 0.04 mU/ng |

Example 6

Generation of Stable Mammalian Cell Lines Expressing Hyperglycosylated Human Coagulation Factor IX Chinese hamster ovary (CHO-K1) cells were co-transfected with pSV2-neo containing the neomycin resistance gene and pGB024 encoding the hyperglycosylated FIX-T172N-K228N-I251T-A262T variant using FuGENE 6 Transfection Reagent (Roche). Transfected cells were selected with 600 µg/ml G418 and cloned by limiting dilution. Resistant clones were screened by testing cell culture supernatants for coagulation factor IX antigen by ELISA, and 12 coagulation factor IX producing cell lines were expanded. Medium from tissue culture flasks with the 12 clones was analysed for coagulation factor IX antigen by ELISA and for coagulation factor IX activity by activated partial thromboplastin time (APTT) assay in an ACL 9000 clotting instrument (Instrumentation Laboratory) using reagent from the same manufacturer. The specific activities of the coagulation factor IX proteins in the media were calculated by combining the ELISA and clot assay data as shown in Table 7. Clone 15 was seeded in roller bottles, and the hyperglycosylated FIX-T172N-K228N-I251T-A262T variant was purified from medium harvested from the roller bottles.

TABLE 7

Characterization of hyperglycosylated human coagulation factor IX in medium from CHO-K1 cell lines transfected with pGB024

| Clone | Factor IX activity (APTT assay) | FIX antigen (ELISA) | Specific activity |
|---|---|---|---|
| 2 | 0.019 U/ml | 988 ng/ml | 0.019 mU/ng |
| 6 | 0.013 U/ml | 1118 ng/ml | 0.012 mU/ng |
| 7 | 0.009 U/ml | 662 ng/ml | 0.014 mU/ng |
| 8 | 0.008 U/ml | 606 ng/ml | 0.013 mU/ng |
| 9 | 0.014 U/ml | 500 ng/ml | 0.021 mU/ng |
| 10 | 0.048 U/ml | 960 ng/ml | 0.050 mU/ng |
| 11 | 0.023 U/ml | 996 ng/ml | 0.023 mU/ng |
| 12 | 0.011 U/ml | 622 ng/ml | 0.018 mU/ng |
| 15 | 0.029 U/ml | 722 ng/ml | 0.040 mU/ng |
| 16 | 0.019 U/ml | 360 ng/ml | 0.052 mU/ng |
| 17 | 0.009 U/ml | 990 ng/ml | 0.009 mU/ng |
| 18 | 0.019 U/ml | 526 ng/ml | 0.036 mU/ng |

Example 7

Figure 4:
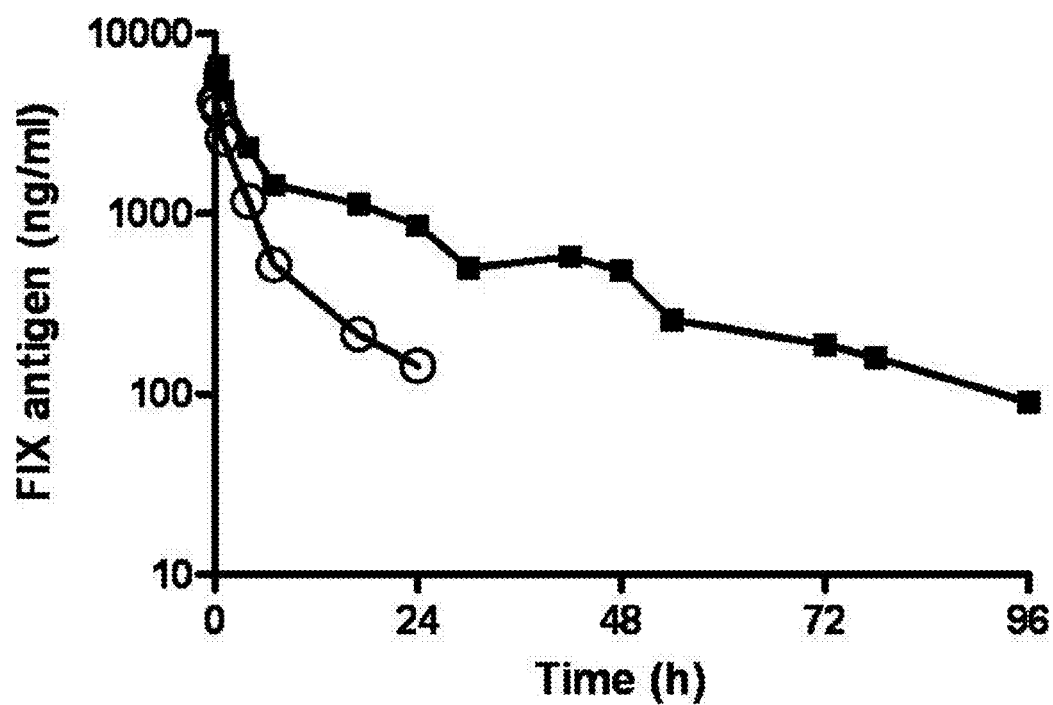
FIG. 4 describes the mean FIX antigen concentrations versus time in plasma of coagulation factor IX knock-out mice injected with the hyperglycosylated recombinant human coagulation factor IX variant FIX-T172N-K228N-I251T-A262T (full squares) or recombinant wild-type human coagulation factor IX (open circles) (Example 7).

Comparison of the Pharmacokinetic Properties of Hyperglycosylated Human Coagulation Factor IX with those Wild-type Human Coagulation Factor IX Hyperglycosylated human coagulation factor IX (FIX-T172N-K228N-I251T-A262T) and human wild-type coagulation factor IX (BeneFIX®, Wyeth) were diluted in 10 mM histidine, 0.26 M glycine, 1% sucrose, 0.005 Tween80, pH 6.8 to a concentration of 0.2 mg/ml (FIX-T172N-K228N-I251T-A262T) or 0.4 mg/ml (wild-type coagulation factor IX). Each compound was administered via the tail vein of 15 coagulation factor IX knock-out mice at a dose of 1.0 mg/kg (FIX-T172N-K228N-I251T-A262T) or 1.5 mg/kg (wild-type coagulation factor IX). At various time points after administration, 3 mice were anaesthetized and blood was sampled from the orbital plexus. Three blood samples were drawn from each mouse and after the third blood sample, the mice were euthanized by cervical dislocation. Blood samples were stabilized with sodium-citrate and diluted 5 times in 50 mM HEPES, 150 nM NaCl, 0.5% bovine serum albumin, pH 7.4. The stabilized and diluted blood was centrifuged to pellet blood cells. The resulting plasma samples were analyzed for FIX antigen by ELISA using compound specific standard curves. The mean FIX antigen concentrations versus time are shown in FIG. 4. The estimated pharmacokinetic parameters are listed in Table 8. The data demonstrate prolongation of the in vivo half-life and reduced clearance of the hyperglycosylated FIX-T172N-K228N-I251T-A262T variant as compared to wild-type coagulation factor IX.

TABLE 8

Pharmacokinetic parameters in coagulation factor
IX knock-out mice determined by ELISA

| Compound | Terminal half-life | Clearance | Mean residence time |
|---|---|---|---|
| Wild-type FIX (BeneFIX ®, Wyeth) | 9 h | 81 ml/h/kg | 8 h |
| FIX-T172N-K228N-I251T-A262T | 22 h | 15 ml/h/kg | 27 h |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Preferred Features of the Invention:

1. A human factor IX polypeptide analogue having one or more mutations wherein said mutations result in the introduction of one or more glycosylation sites in the polypeptide.

2. A polypeptide as defined in clause 1 wherein said glycosylation comprises N-glycosylation.

3. A polypeptide as defined in clause 1 wherein the one or more mutations result in an increased molecular weight of the factor IX polypeptide analogue when compared with the wild-type polypeptide.

4. A polypeptide as defined in clause 1 wherein the one or more mutations result in a more acidic isoelectric point for the factor IX polypeptide analogue when compared with the wild-type polypeptide.

5. A polypeptide as defined in clause 1 wherein the one or more mutations result in no more than a 0, 1, 2, 5, 10, 20, 50 or 100 fold reduction of proteolytic activity and/or clot activity of the factor IX polypeptide analogue when compared with the wild-type polypeptide.

6. A polypeptide as defined in clause 5 wherein the one or more mutations result in no more than a 0 fold reduction of proteolytic activity and/or clot activity of the factor IX polypeptide analogue when compared with the wild-type polypeptide.

7. A polypeptide as defined in clause 1 or clause 2 wherein said one or more mutations comprise incorporation of one or more N-X-S/T motifs.

8. A polypeptide as defined in clause 7 wherein the one or more N-X-S/T motifs are established at positions where said residue intended to be an "N" residue has a relative side-chain surface accessibility of more than 25%.

9. A polypeptide as defined in clause 8 wherein said one or more mutations are selected from one or more of the following:

Y1N, S3N+K5S/T, G4N+L6S/T, F9N+Q11S/T, V10N+G12S/T, G12N+L14S/T, R16N+C18S/T, K22N, R29N+V31S/T, T35N+R37S/T, R37N, T39N+F41S/T, F41N+K43S/T, W42N+Q44S/T, Q44N+V46S/T, V46N+G48S/T, D47N+D49S/T, G48N+Q50S/T, D49N+C51S/T, Q50N+E52S/T, E52N+N54T, S53N+P55S/T, C56S/T, L57N+G59S/T, G60S/T, S61N+K63S/T, K63N+D65S/T, D65N+N67S/T, I66N+S68S/T, Y69S/T, Y69N+C71S/T, S68N+E70S/T, E70N+W72S/T, W72N+P74S/T, P74N+G76S/T, F77N+G79S/T, G79N+N81S/T, K80N+C82S/T, E83S/T, E83N+D85S/T, L84N+V86S/T, D85N, V86N+C88S/T, T87N+N89S/T, I90N+N92S/T, K91S/T, I90N+N92S/T, K91N+G93S/T, R94S/T, R94N+E96S/T, K100N, A103S/T, S102N+D104S/T, A103N+N105S/T, D104N+K106S/T, V107S/T, K106N+V108S/T, V108N+V110S/T, S110N, E113N+Y115S/T, G114N+R116S/T, R116N+A118S/T, E119N+Q121S/T, K122S/T, Q121N+S123S/T, K122N+C124S/T, S123N+E125S/T, E125N+Al25S/T, P126N+V128S/T, V128N+F130S/T, P129N+P131S/T, F130N+C132S/T, R134N, V135N+V137S/T, S136N, S138N, Q139N, T140N+L142S/T, S141N+L143S/T, K142N, A146N+A148S/T, E147N+V149S/T, A148N+F150S/T, V149N+P515S/T, F150N+D152S/T, P151N+V153S/T, D152N+D154S/T, V153N+Y155S/T, D154N+V156S/T, Y155N+N157S/T, V156N, S158N+E160S/T, T159N+A161S/T, E160N+E162S/T, A161N, E162N+I164S/T, T163N+L165S/T, I164N+D166S/T, L165N+N167S/T, D166N+I168S/T, I168N+Q170S/T, T169N, Q170N, S171N+Q173S/T, T172N, Q173N+F175S/T, S174N+N176S/T, F175N+D177S/T, F178S/T, D177N, F178N+R180S/T, T179N+V181S/T, R180N+V182S/T, G183+E185S/T, E185N+A187S/T, D186N+K188S/T, K188N+G190S/T, P189N+Q181S/T, K201N+D203S/T, V202N+A204S/T, D203N+F205S/T, E213N+W215S/T, E224N+G226S/T, T225N+V227S/T, G226N+K228S/T, K228N, E239N, E240N+E242S/T, T241N+H243S/T, H243N+E245S/T, K247N+N249S/T, I251S/T, I251N+I253S/T, R252N+I254S/T, I253N+P255S/T, P255N+H257S/T, H257N+Y259S/T, N260S/T, A262S/T, A261N+I263S/T, A262N+N264S/T, I263N+K265S/T, K265N+N267S/T, A266N+H268S/T, D276N+P278S/T, P278N+V280S/T, E277N+L279S/T, V280N+N282S/T, Y284S/T, S283N+V285S/T, Y284N, D292N+K294S/T, K293N+Y295S/T, E294N, F299S/T, I298N+L300S/T, K301N+G303S/T, F302N, G303N+G305S/T, S304N+Y306S/T, Y306N+S308S/T, R312N+F314S/T, F314N+K316S/T, H315N+G317S/T, K316N+R138S/T, G317N, R318N+A320S/T, S319N+L321S/T, L321N+L323S/T, V322N+Q324S/T, Y325N+R327S/T, R327N+P329S/T, P329N+V331S/T, L330N+D332S/T,

D332N+A334S/T, R333N, A334N+C336S/T, T335N+L337S/T, L337N, R338N, K341N, F342N+I344S/T, T343N+Y345S/T, Y345N+N347S/T, M348S/T, H354N+G356S/T, E355N+G357S/T, G357N+D359S/T, R358N, Q362N+D364S/T, E372N+E374S/T, E374N, G375N, E388N+A390S/T, M391N+G393S/T, K392N+K394S/T, G393N+Y395S/T, K394N+G396S/T, R403N+V405S/T, I408S/T, K409N+K411S/T, E410N, K411N+K413S/T, and K413N.

10. A polypeptide as defined in clause 7 wherein the one or more N-X-S/T motifs are established at positions where said residue intended to be an "N" residue has a relative side-chain surface accessibility of more than 50%.

11. A polypeptide as defined in clause 10, wherein said one or more mutations are selected from one or more of the following:

Y1N, S3N+K5S/T, G4N+L6S/T, F9N+Q11S/T, V10N+G12S/T, K22N, R37N, Q44N+V46S/T, V46N+G48S/T, D47N+D49S/T, G48N+Q50S/T, Q50N+E52S/T, E52N+N54T, S53N+P55S/T, C56S/T, L57N+G59S/T, S61N+K63S/T, 166N+S68S/T, Y69S/T, S68N+E70S/T, E70N+W72S/T, W72N+P74S/T, P74N+G76S/T, K80N+C82S/T, L84N+V86S/T, T87N+N89S/T, K91S/T, 190N+N92S/T, K91N+G93S/T, R94N+E96S/T, K100N, A103S/T, S102N+D104S/T, A103N+N105S/T, D104N+K106S/T, V107S/T, K106N+V108S/T, V108N+V110S/T, E113N+Y115S/T, R116N+A118S/T, E119N+Q121S/T, K122S/T, Q121N+S123S/T, S123N+E125S/T, E125N+A125S/T, P129N+P131S/T, S138N, T140N+L142S/T, S141N+L143S/T, K142N, A146N+A148S/T, E147N+V149S/T, A148N+F150S/T, V149N+P515S/T, F150N+D152S/T, P151N+V153S/T, D152N+D154S/T, V153N+Y155S/T, D154N+V156S/T, Y155N+N157S/T, V156N, S158N+E160S/T, T159N+A161S/T, E160N+E162S/T, A161N, E162N+I164S/T, T163N+L165S/T, I164N+D166S/T, L165N+N167S/T, D166N+I168S/T, I168N+Q170S/T, T169N, Q170N, S171N+Q173S/T, T172N, Q173N+F175S/T, S174N+N176S/T, F175N+D177S/T, F178S/T, D177N, F178N+R180S/T, T179N+V181S/T, R180N+V182S/T, G183+E185S/T, E185N+A187S/T, D186N+K188S/T, K188N+G190S/T, P189N+Q181S/T, K201N+D203S/T, V202N+A204S/T, D203N+F205S/T, E224N+G226S/T, T225N+V227S/T, G226N+K228S/T, K228N, E239N, E240N+E242S/T, T241N+H243S/T, H243N+E245S/T, K247N+N249S/T, I251S/T, R252N+I254S/T, P255N+H257S/T, H257N+Y249S/T, A262S/T, A261N+I263S/T, A262N+N264S/T, 1263N+K265S/T, K265N+N267S/T, E277N+L279S/T, V280N+N282S/T, D292N+K294S/T, K293N+Y295S/T, E294N, K301N+G303S/T, G303N+G305S/T, F314N+K316S/T, K316N+R138S/T, R318N+A320S/T, L321N+L323S/T, R327N+P329S/T, D332N+A334S/T, R333N, R338N, K341N, F342N+I344S/T, T343N+Y345S/T, H354N+G356S/T, E355N+G357S/T, G357N+D359S/T, E372N+E374S/T, E374N, G375N, M391N+G393S/T, K392N+K394S/T, G393N+Y395S/T, I408S/T, E410N, and K413N.

12. A polypeptide as defined in clause 1, wherein said one or more mutations are selected from one or more of the following:

Y1N, K22N, R37N, C56S/T, G60S/T, Y69S/T, E83S/T, D85N, K91S/T, R94S/T, K100N, A103S/T, V107S/T, S110N, K122S/T, R134N, S136N, S138N, Q139N, K142N, V156N, A161N, T169N, Q170N, T172N, F178S/T, D177N, K228N, E239N, 12515/T, N260S/T, A262S/T, Y284S/T, Y284N, E294N, F299S/T, F302N, G317N, R333N, L337N, R338N, K341N, M348S/T, G358N, E374N, G375N, 14085/T, E410N, and K413N.

13. A polypeptide as defined in clause 1, wherein said one or more mutations are selected from one or more of the following:

T172N, K228N, I251T and A262T.

14. A glycosylated human factor IX polypeptide analogue, wherein said polypeptide is glycosylated at one or more positions other than N157 or N167 relative to wild-type human factor IX polypeptide.

15. A polypeptide as defined in clause 14 wherein said polypeptide is glycosylated at one or more positions selected from one or more of the following:

Y1, S3, G4, F9, V10, Q11, G12, R16, K22, R29, T35, R37, T39, F41, W42, Q44, V46, D47, G48, D49, Q50, E52, S53, N54, L57, N58, G59, S61, K63, D65, 166, N67, S68, Y69, E70, W72, P74, F77, G79, K80, N81, E83, L84, D85, V86, T87, N89, I90, K91, N92, R94, K100, N101, S102, A103, D104, N105, K106, V108, S110, E113, G114, R116, E119, N120, Q121, K122, S123, E125, P126, V128, P129, F130, R134, V135, S136, S138, Q139, T140, S141, K142, A146, E147, A148, V149, F150, P151, D152, V153, D154, Y155, V156, S158, T159, E160, A161, E162, T163, I164, L165, D166, I168, T169, Q170, S171, T172, Q173, S174, F175, N176, D177, F178, T179, R180, G183, E185, D186, K188, P189, K201, V202, D203, E213, E224, T225, G226, K228, E239, E240, T241, H243, K247, N249, I251, R252, I253, P255, H257, N258, N260, A261, A262, I263, N264, K265, A266, D276, E277, P278, V280, N282, S283, Y284, D292, K293, E294, N297, I298, K301, F302, G303, S304, Y306, R312, F314, H315, K316, G317, R318, S319, L321, V322, Y325, R327, P329, L330, D332, R333, A334, T335, L337, R338, K341, F342, T343, Y345, N346, H354, E355, G357, R358, Q362, E372, E374, G375, E388, M391, K392, G393, K394, R403, N406, K409, E410, K411, and K413.

16. A polypeptide as defined in clause 14 wherein said polypeptide is glycosylated at one or more positions selected from one or more of the following:

Y1, S3, G4, F9, V10, Q11, K22, R37, Q44, V46, D47, G48, Q50, E52, S53, N54, L57, G59, S61, I66, N67, S68, E70, W72, P74, K80, L84, T87, N89, I90, K91, R94, K100, N101, S102, A103, D104, N105, K106, V108, E113, R116, E119, N120, Q121, S123, E125, P129, S138, T140, S141, K142, A146, E147, A148, V149, F150, P151, D152, V153, D154, Y155, V156, S158, T159, E160, A161, E162, T163, I164, L165, D166, I168, T169, Q170, S171, T172, Q173, S174, F175, N176, D177, F178, T179, R180, G183, E185, D186, K188, P189, K201, V202, D203, E224, T225, G226, K228, E239, E240, T241, H243, K247, N249, R252, P255, H257, N260, A261, A262, I263, K265, E277, V280, D292, K293, E294, K301, G303, F314, K316, R318, L321, R327, D332, R333, R338, K341, F342, T343, H354, E355, G357, E372, E374, G375, M391, K392, G393, N406, E410, and K413.

17. A polypeptide as defined in clause 14 wherein said polypeptide is glycosylated at one or more positions selected from one or more of the following:

Y1, K22, R37, N54, N58, N67, N81, D85, N89, N92, K100, N101, N105, S110, N120, R134, S136, S138, Q139, K142, V156, A161, T169, Q170, T172, N176, D177, K228, E239, N249, N258, N260, N282, Y284, E294, N297, F302, G317, R333, L337, R338, K341, N346, R358, E374, G375, N406, E410, and K413.

18. A polypeptide as defined in clause 14 wherein said polypeptide is glycosylated at one or more positions selected from one or more of the following:

T172, K228, N249 and N260.

19. A polypeptide as defined in any of clauses 14 to 18 wherein the hyperglycosylated polypeptide comprises at least one glycan.

20. A method of treating hemophilia which comprises administering to a patient a therapeutically effective amount of a polypeptide as defined in any preceding clauses.

21. A polypeptide as defined in any of clauses 1 to 19 for use in the treatment of hemophilia.

22. Use of a polypeptide as defined in any of clauses 1 to 19 in the manufacture of a medicament for the treatment of hemophilia.

23. A pharmaceutical composition comprising a polypeptide as defined in any of clauses 1 to 19 for use in the treatment of hemophilia.

24. A process for preparing a polypeptide analogue as defined in any of clauses 1 to 19 which comprises the steps of:
(a) site directed mutagenesis of human factor IX to incorporate one or more N-X-S/T motifs into DNA encoding human factor IX;
(b) transfection of the resultant nucleic construct into a producer cell; and
(c) purification of the polypeptide analogue from the transfected producer cells.

25. A nucleic acid construct encoding the human factor IX polypeptide analogue as defined in any of clauses 1 to 19.

26. A recombinant vector comprising a nucleic construct as defined in clause 25.

27. A cell transfected with a vector as defined in clause 26.

28. A cell as defined in clause 27 which is a eukaryotic producer cell.

29. A cell as defined in clause 27 or clause 28 which is a mammalian cell, such as a Chinese Hamster Ovary (CHO) cell (e.g CHO-K1) or a human embryonal kidney (HEK) cell (e.g. HEK293F).

30. A pharmaceutical formulation comprising a polypeptide as defined in any of clauses 1 to 19.

The invention claimed is:

1. A human coagulation factor IX polypeptide of having the amino acid sequence according to SEQ ID NO: 1 with four mutations T172N+K228N+I251T+A262T, wherein said mutations result in the introduction of four glycosylation sites in the human coagulation factor IX polypeptide.

2. A pharmaceutical composition comprising the human coagulation factor IX polypeptide of claim 1.

3. A process for preparing the human coagulation factor IX polypeptide of claim 1 comprising the steps of:

(a) performing site directed mutagenesis of a polynucleotide encoding a human factor IX polypeptide to incorporate one or more N-X-S/T motifs into the polynucleotide, thereby forming a nucleic acid construct;
(b) transfecting the nucleic acid construct into a producer cell; and
(c) purifying the human coagulation factor IX polypeptide of claim 1 from the transfected producer cell.

4. A nucleic acid construct encoding the human coagulation factor IX polypeptide of claim 1.

* * * * *